United States Patent [19]

Skrabal et al.

[11] Patent Number: 5,325,867
[45] Date of Patent: Jul. 5, 1994

[54] DEVICE FOR WITHDRAWING BODY FLUIDS

[75] Inventors: Falko Skrabal, Graz; Erich Kleinhappl, Weinitzen; Helmut List, Graz, all of Austria

[73] Assignee: AVL Medical Instruments AG, Schaffhausen, Switzerland

[21] Appl. No.: 820,591

[22] PCT Filed: May 21, 1991

[86] PCT No.: PCT/AT91/00066
§ 371 Date: Jan. 24, 1992
§ 102(e) Date: Jan. 24, 1992

[87] PCT Pub. No.: WO91/18551
PCT Pub. Date: Dec. 12, 1991

[30] Foreign Application Priority Data

Jun. 1, 1990 [AT] Austria ............... 1208/90

[51] Int. Cl.$^5$ .............................................. A61B 5/00
[52] U.S. Cl. .................................. 128/765; 128/766; 604/30; 604/152; 604/153
[58] Field of Search ............... 128/760, 762, 763, 764, 128/765, 766, 767, 771; 604/27, 36, 37, 38, 39, 43, 44, 48, 65, 67, 113, 114, 131, 132, 133, 149, 151, 153, 51, 52, 53, 19, 152

[56] References Cited

U.S. PATENT DOCUMENTS

| 1,553,859 | 9/1925 | Hein | 604/36 |
|---|---|---|---|
| 3,512,517 | 5/1970 | Kadish et al. | 604/27 |
| 3,765,402 | 10/1973 | Grabhorn | |
| 3,890,955 | 6/1975 | Elliott | 128/764 |
| 4,008,717 | 2/1977 | Kowarski | |
| 4,077,395 | 3/1978 | Woolner | 128/762 |
| 4,249,923 | 2/1981 | Walda | 62/394 |
| 4,676,256 | 6/1987 | Golden | 128/762 |
| 4,879,098 | 11/1989 | Oberhardt et al. | 422/101 |
| 4,936,314 | 6/1990 | Kasai et al. | 128/764 |
| 5,029,584 | 7/1991 | Smith | 128/638 |
| 5,066,283 | 11/1991 | Skrabal | 604/152 |
| 5,123,477 | 6/1992 | Tyler | 165/2 |

FOREIGN PATENT DOCUMENTS

| 0223758 | 5/1987 | European Pat. Off. | |
|---|---|---|---|
| 8002706 | 12/1980 | PCT Int'l Appl. | 128/762 |
| 9115153 | 10/1991 | PCT Int'l Appl. | 128/766 |

OTHER PUBLICATIONS

International Publication No. WO 89/00397 dated Jan. 26, 1989 to Falko Skrabal.

Primary Examiner—Stephen C. Pellegrino
Assistant Examiner—Guy V. Tucker
Attorney, Agent, or Firm—Watson, Cole, Grindle & Watson

[57] ABSTRACT

A device for the sampling of body fluids using a hollow needle (6), is provided with a storage system (3) with several separate sample containers (4) placed on a movable carrier (9). The containers (4) which are sealed by puncturable membranes (5) so as to be gas-tight, will receive collected fractions of the body fluid at given intervals, a device (7) connected to a control unit (2) being provided, by which the hollow needle (6) is positioned over each sample container (4) in turn and is inserted through the membrane (5) into the sample container. The sampling device 1 is configured as a two-channel cannula (18), one (19) of whose channels is connected via a first connecting tube (25) to the hollow needle (6) used for insertion into the sample containers (4), while its other channel (20) is connected via a second connecting tube (26) to a pump (8'; 21) operated by the control unit (2). In their unused state the individual sample containers (4) are filled within an amount of gas or gas mixture whose volume at atmospheric pressure is smaller than that of the body fluid to be received.

20 Claims, 3 Drawing Sheets

DEVICE FOR WITHDRAWING BODY FLUIDS

BACKGROUND OF THE INVENTION

This invention relates to a device for the sampling of body fluids, such as blood, urine, or tissue fluid, comprising a sampling unit connected to a hollow needle, and a storage system with several separate sample containers placed on a movable carrier, which are sealed so as to be gas-tight by means of puncturable membranes, and which are intended to receive collected fractions of the body fluid at given intervals, a device connected to a control unit being provided, which will permit the hollow needle to be positioned over each sample container in turn and to be inserted into the sample container through the membrane.

In medical applications it is often necessary to sample biological fluids, such as human or animal blood, urine, or tissue fluid, either continuously or intermittently. It would be desirable if such fluids could be collected 24 hours a day, i.e. during both day-time and night-time, without disturbing the patient's sleep, in order to obtain unbiased test results.

For such applications a new method is specified in WO 89/00397. Via a roller pump a few microliters of blood or tissue fluid (the latter being obtained by delivering a perfusion fluid into the tissue) are collected in capillary tubes, and a system of valves is used to establish a correspondence between the fluid samples and their withdrawal times.

This system requires a complex mechanism of valves, which will increase teh weight of the apparatus amongst others. In the individual sections of the capillary system the blood column may come to a halt, which might lead to the formation of clots in the system.

A device of the afore-mentioned type is presented in EP-A 0 223 758, for example. The apparatus for the handling of small fluid samples described there includes a rotatable fixture carrying a number of sample containers receiving the fluid samples by means of a hollow needle. The hollow needle is connected by a tube to a sampling unit, or rather, sampling needle (not discussed in detail) used for drawing the sample. The relative movement between hollow needle and sample container is provided by a special device permitting the needle to be properly inserted into the sample containers. For better protection of the needle its fitting is provided with a pressure sensor stopping any further movement of the needle if the axial forces exceed a given limit. If membrane-sealed sample containers are used, attention should be paid to the change in interior pressure during sample manipulation. The solution to this problem offered in EP-A 0 223 758, i.e., a needle with two bores, one of which provides the necessary pressure relief, is characterized by the disadvantage that sample components also may be released through this opening. This may lead to contamination of equipment of staff.

It is an object of the invention to develop a compact device on the basis of the afore-mentioned design, which may be attached to the patient even for prolonged periods of time, and will permit fluid samples, such as blood, urine, or tissue fluid, to be gathered safely and stored until further processing, regardless of the physical location of the device.

SUMMARY OF THE INVENTION

In the invention this object is achieved by providing a two-channel cannula as a sampling device, one of whose channels is connected via a fist connecting tube to the hollow needle used for insertion into the sample containers, while the other channel is connected via a second connecting tube to a pump operated by the control unit, and further by providing that the individual sample containers contain an amount of gas or gas mixture before use, whose volume is smaller at atmospheric pressure than the volume of the body fluid to be received.

A first, very simple variant provides that the sample containers have rigid walls, and that the pressure prevailing inside the containers be lower than the ambient pressure, thus developing a pumping effect, and that the connecting tube between the two-channel cannula and the hollow needle be provided with a metering unit. Via the metering unit, for example, a metering valve, the desired fluid flow can be adjusted. This variant does not require the use of a pump handling fluid transport, which will further simplify the device.

Another variant of the invention is characterized by the individual sample containers being configured as evacuated, deformable vessels, and by the connecting tube between the two-channel cannula and the hollow needle being provided with a pump, preferably a peristaltic pump, for handling the body fluid.

For safe storage of the fluid fractions during the period between withdrawal and subsequent analysis, such that unbiased test results may be obtained, it is provided by the invention that the sample containers placed on the movable carrier be encased by a heat-insulating housing with openings in its cover for the passage of the hollow needle, and that the housing contain a temperature sensor connected to the control unit as well as a cooling medium.

It will be of advantage if the heat-insulating housing including the sample containers is configured so as to be detachable from the remaining device. While the collected fluid samples are stored in the heat-insulating housing until they are further processed, i.e., analysed, a new housing with empty containers may be instantaneously attached to the device and the sampling process may be continued without major interruption.

If sampling takes place in blood vessels, it will be an advantage if the channel of the two-channel cannula, which is leading to a pump, is connected to a drug pump, whose drive is connected to the control unit. The drug pump may contain heparin, for instance, and the heparin released at the tip of the needle from one channel, will immediately drain into the other channel of the needle, such that only small quantities of heparin will enter the body and the formation of blood clots in the tube system of the apparatus is effectively prevented.

It is provided in an enhanced variant of the invention that the device be furnished with an additional drug pump, preferably a syringe, whose drive is in connection with the control unit. This type of device will permit investigations of the action of a particular preparation and of the change of drug levels in the blood over time. By means of the syringe a drug may be administered in accurately determined doses, its pharmacokinetics permitting conclusions as to the body functions.

If samples of tissue fluid are to be drawn directly from the tissue, a further variant of the invention provides that the second connecting tube lead into a container for a perfusion fluid, and that the first connecting tube, which leads to the hollow needle, be passed through a peristaltic pump in the direction of suction, while the second connecting tube be passed through this pump in pumping direction.

According to the invention the wall of the outer channel of the two-channel cannula may have a perforation, preferably a number of perforations.

It is finally provided in yet another variant of the invention that the wall of the outer channel of the two-channel cannula be configured, at least in part, as a diffusion path.

Following is a more detailed description of the invention as illustrated by the attached drawings.

DETAILED DESCRIPTION OF THE PREFERRED EMBODIMENTS

Figure 1:
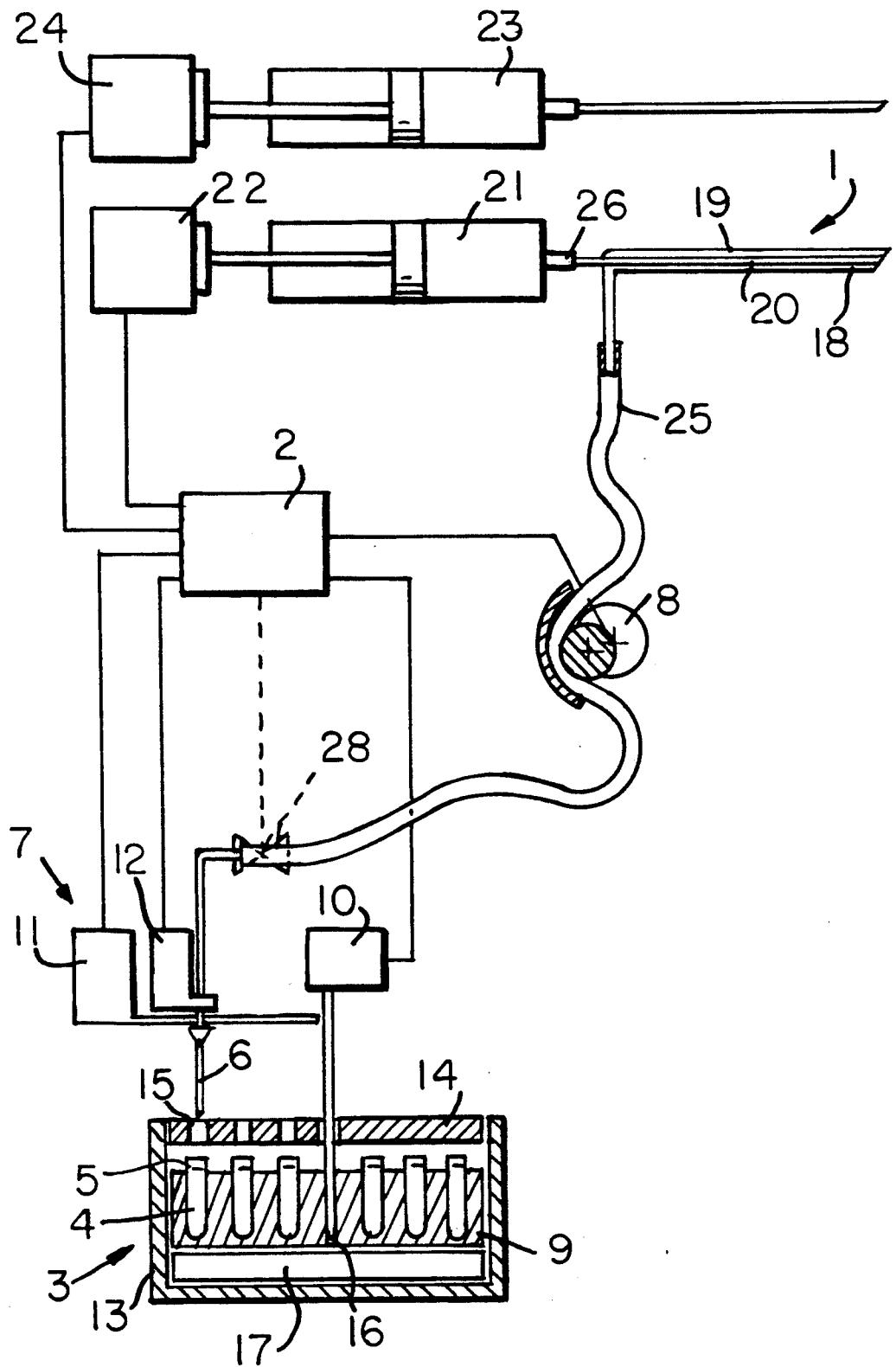
FIG. 1 is a schematic diagram of a device according to the invention depicting the sampling unit, control unit and storage system.

The main components of the device for the withdrawal of body fluids presented in FIG. 1 are a sampling unit 1, a control or data input unit 2, and a storage system 3. The storage system 3 includes a number of sample containers 4 arranged in several concentric circles, which containers 4 are sealed by puncturable membranes 5 so as to be gas-tight. By means of a device 7 connected to the control unit 2, a hollow needle 6 connected to the sampling unit 1 via a connecting tube is positioned over each of the sample containers 4 in turn and inserted into the container 4 through the membrane 5.

The individual sample containers 4 either may have rigid walls-the pressure inside them being lower than the ambient pressure-, or may be configured as evacuated, deformable vessels. In either instance the individual sample containers 4 contain a quantity of gas or gas mixture before use, having a volume at atmospheric pressure which is smaller than the volume of the body fluid to be received. In this way the containers need not be evacuated upon filling, and the apparatus will be ready for use regardless of where it is situated. At the same time sample components are effectively prevented from escaping.

Figure 3:
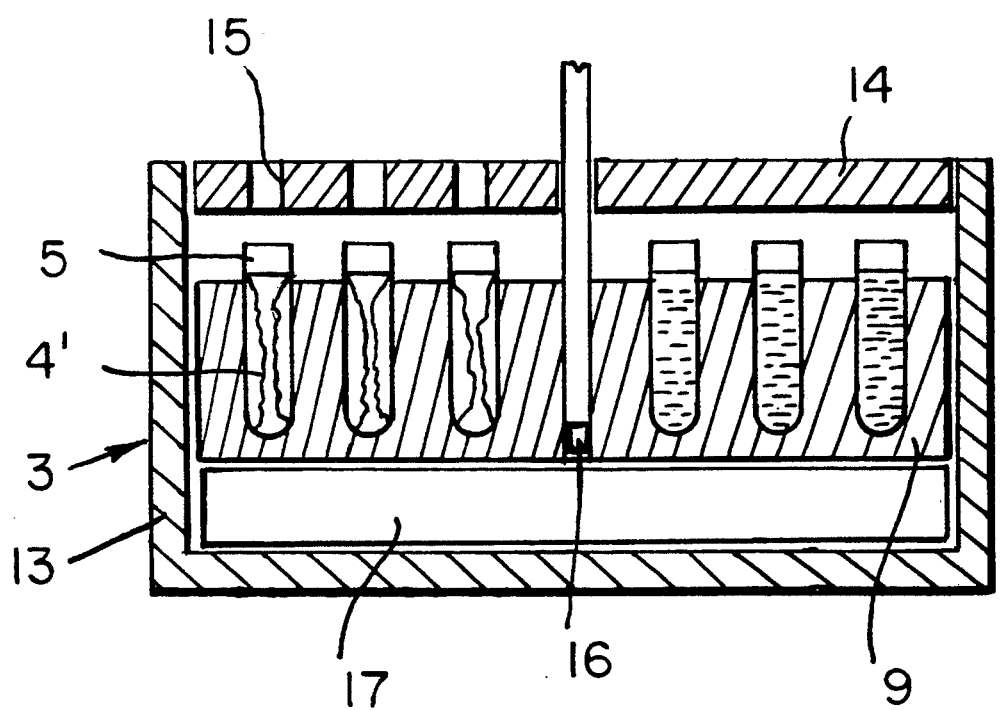
FIG. 3 shows a storage system for an embodiment of the device according to the present invention which comprises deformable, evacuated vessels as sample containers.

FIG. 3 shows a storage system for an embodiment of the device according to the present invention which comprises deformable, evacuated vessels 4' as sample containers. The pressure within each vessel before being punctured is less than the atmospheric pressure.

Between the sampling unit 1 and the hollow needle 6 a metering unit is installed, which is configured as a peristaltic pump 8 in FIG. 1. In the instance of rigid-wall sample containers 4 developing a pumping effect due to their reduced interior pressure, a metering valve 28 could be used instead of the peristaltic pump 8. This metering valve could also be actuated by the control unit 2.

In the variant presented here the movable carrier 9 for the sample containers 4 is configured as a revolving tray encased by a heat-insulating housing 13, which tray has a drive unit 10 connected to the control unit 2. The device 7 used for positioning the hollow needle 6 comprises a first drive element 11 for radial movement of the hollow needle 6, and a second drive element 12 for vertical movement of the hollow needle 6. Both drive elements, 11 and 12, receive signals from the control unit 2.

The heat-insulating housing 13 has a cover 14 with openings 15 through which the hollow needle 6 may be inserted into the sample containers 4. Each of the several tiers of containers is assigned only one opening 15, in order to minimize cooling losses.

The housing 13 contains a temperature sensor 16 connected with the control unit 2 as well as a cooling medium 17. If the permissible maximum temperature is exceeded the electronics of the control unit 2 will trigger an optical or acoustic alarm. In a preferred variant the heat-insulating housing 13 including the sample containers 4 is detachable from the remaining device. By attaching a new housing with empty sample containers the sampling of body fluid may be continued without interruption.

In the variant of FIG. 1 the hollow needle 6 to be inserted into the sample containers 4 is connected via a first connecting tube 25 to the outer channel 19 of a sampling device 1 configured as a two-channel cannula 18, while the inner channel 20 of the cannula 18 has a connecting tube 26 into a drug pump, for example, a heparin pump 21. The drive 22 of the heparin pump is also connected to the control unit 2. Because of the precise dose of heparin, which is released at the tip of the two-channel cannula 18 and is immediately drained by the vacuum in the outer cannula 19, the blood is prevented from clotting in the connecting tube 25 leading to the hollow needle 6. Blood clotting could also be prevented by coating the connecting tube 25 with a special anticoagulant.

Via the control unit 2 the device can also be connected to a second drug pump 23 and its drive 24. The drug syringe will permit the continual administering of a precisely metered quantity of a drug, whose pharmacokinetics will permit conclusions as regards the body functions.

In addition, the control unit or input unit 2 will enable the patient to enter a given code or to press a key in case of an unexpected event. In this way the device is caused by the control unit to fill certain sample containers out of turn, which then may be processed separately. After this special turn the device will automatically return to normal operation.

Figure 2:
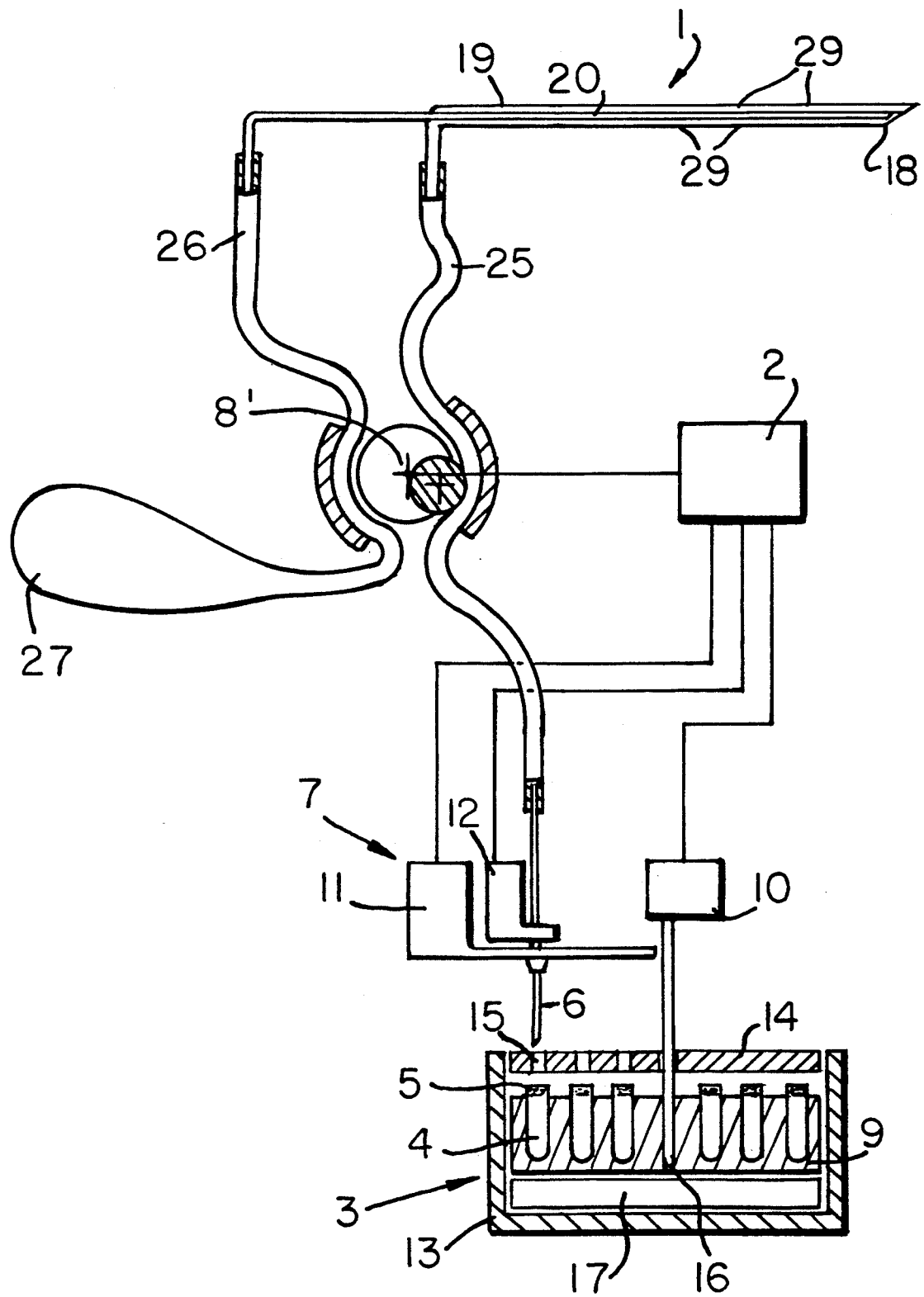
FIG. 2 is a schematic diagram of a variant of the device of FIG. 1 particular suited for tissue perfusion and which shows a container for perfusion fluid and an associated pump.

The variant shown in FIG. 2 is particularly well suited for tissue perfusion, in which a perfusion fluid is introduced in the the tissue and pumped out after a short phase of equilibration (cf. WO 89/00397 referred to before). In this case the hollow needle 6 used for insertion into the sample container 4 is connected to channel 19 of the two-channel cannula 18 by means of the first connecting tube 25, and the other channel 20 of the cannula 18 is connected to a container 27 for a perfusion fluid by means of the second connecting tube 26. The first connecting tube 25 may be passed through a peristaltic pump 8' in the direction of suction, while the second connecting tube 26 may be passed through the same pump 8' in pumping direction. The outer wall of the cannula 18 is provided with perforations 29 enlarging the area of contact with the tissue.

For special applications the wall of the outer channel 19 of the cannula 18 may partly be configured as a diffusion path.

We claim:

1. A device for withdrawing body fluids, such as blood, urine and tissue fluid, comprising a sampling unit connected to a hollow needle, and a storage system comprising a heat-insulating housing having openings through which said hollow needle may pass, wherein said heat-insulating housing encases several separate sample containers placed on a movable carrier, each said sample container being sealed by means of a puncturable membrane so as to be gas-tight, said sample containers intended to receive fractions of said body fluid collected at given intervals, said device also comprising a control unit being provided to control the positioning of said hollow needle over each of said sample containers in turn and to control the insertion of said hollow needle into each sample container through said puncturable membrane, wherein said sampling unit is configured as a two-channel cannula, a first of said channels being connected via a first connecting tube to said hollow needle and a second of said channels being connected via a second connecting tube to a pump operated by said control unit, and wherein said sample containers have rigid walls, and wherein the pressure prevailing inside said sample containers is lower than the ambient pressure.

2. A device according to claim 1, wherein said first connecting tube between said two-channel cannula and said hollow needle is provided with a metering unit.

3. A device according to claim 1, wherein said first connecting tube between said two-channel cannula and said hollow needle is provided with a pump.

4. A device according to claim 1, wherein said heatinsulating housing contains a cooling medium and a temperature sensor connected to said control unit.

5. A device according to claim 1, wherein said heat-insulating housing including said sample containers is detachable from said sampling unit and said hollow needle.

6. A device according to claim 1, wherein said pump connected to said second channel of said two-channel cannula is a drug pump including a drive is connected to said control unit.

7. A device according to claim 6, comprising an additional drug pump having a drive which is connected to said control unit.

8. A device according to claim 1, wherein said pump is a peristaltic pump, wherein said second connecting tube is connected to a container for a perfusion fluid, and wherein said first connecting tube is passed through said peristaltic pump in a direction of suction, and said second connecting tube is passed through said peristaltic pump in a pumping direction.

9. A device according to claim 8, wherein the wall of said first channel of said two-channel cannula is configured, at least in part, as a diffusion path.

10. A device according to claim 8, wherein the wall of said first channel of said two-channel cannula has a number of perforations.

11. A device for withdrawing body fluids, such as blood, urine and tissue fluid, comprising a sampling unit connected to a hollow needle, and a storage system comprising a heat-insulating housing having openings through which said hollow needle may pass, wherein said heat-insulating housing encases several separate sample containers placed on a movable carrier, each said sample container being sealed by means of a puncturable membrane so as to be gas-tight, said sample containers intended to receive fractions of said body fluid collected at given intervals, said device also comprising a control unit being provided to control the positioning of said hollow needle over each of said sample containers in turn and to control the insertion of said hollow needle into each sample container through said puncturable membrane, wherein said sampling unit is configured as a two-channel cannula, a first of said channels being connected via a first connecting tube to said hollow needle and a second of said channels being connected via a second connecting tube to a pump operated by said control unit, and wherein each said sample container comprises an evacuated deformable vessel.

12. A device according to claim 11, wherein said first connecting tube between said two-channel cannula and said hollow needle is provided with a metering unit.

13. A device according to claim 11, wherein said first connecting tube between said two-channel cannula and said hollow needle is provided with a pump.

14. A device according to claim 11, wherein said heat-insulating housing contains a cooling medium and a temperature sensor connected to said control unit.

15. A device according to claim 14, wherein said heat-insulating housing including said sample containers is detachable from said sampling unit and said hollow needle.

16. A device according to claim 11, wherein said pump connected to said second channel of said two-channel cannula is a drug pump including a which drive is connected to said control unit.

17. A device according to claim 16, comprising an additional drug pump having a drive which is connected to said control unit.

18. A device according to claim 11, wherein said pump is a peristaltic pump, wherein said second connecting tube is connected to a container for a perfusion fluid, and wherein said first connecting tube is passed through said peristaltic pump in a direction of suction, and said second connecting tube is passed through said peristaltic pump in a pumping direction.

19. A device according to claim 18, wherein the wall of said first channel of said two-channel cannula is configured, at least in part, as a diffusion path.

20. A device according to claim 18, wherein the wall of said first channel of said two-channel cannula has a number of perforations.

* * * * *